US00PP28391P3

(12) United States Plant Patent
Klemm et al.

(10) Patent No.: US PP28,391 P3
(45) Date of Patent: Sep. 12, 2017

(54) ***CALIBRACHOA* PLANT NAMED 'KLECA15294'**

(50) Latin Name: ***Calibrachoa* sp.**
Varietal Denomination: KLECA15294

(71) Applicant: Klemm+Sohn GmbH & Co. KG, Stuttgart (DE)

(72) Inventors: Nils Klemm, Stuttgart (DE); Anita Stover, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 86 days.

(21) Appl. No.: 14/998,727

(22) Filed: Feb. 4, 2016

(65) Prior Publication Data

US 2017/0231144 P1 Aug. 10, 2017

(51) Int. Cl.
*A01H 5/02* (2006.01)

(52) U.S. Cl.
USPC ..... Plt./413

(58) Field of Classification Search
USPC ..... Plt./413
See application file for complete search history.

(56) References Cited

PUBLICATIONS

UPOV hit on *Calibrachoa* plant named 'KLECA15294', CA PBR 15-8567, filed Apr. 2, 2015.*

* cited by examiner

*Primary Examiner* — Anne Grunberg
(74) *Attorney, Agent, or Firm* — Bethany R. Roahrig; Barbara Campbell; Cochran Freund & Young, LLC

(57) ABSTRACT

A new *Calibrachoa* plant particularly distinguished by having a pink and red flower color with a yellow throat and a semi-trailing plant habit, is disclosed.

1 Drawing Sheet

Genus and species: *Calibrachoa* sp.
Variety denomination: 'KLECA15294'.

BACKGROUND OF THE NEW PLANT

The present invention comprises a new and distinct variety of *Calibrachoa*, botanically known as *Calibrachoa* sp., and hereinafter referred to by the variety name 'KLECA15294'. 'KLECA15294' originated from an open pollination between the proprietary female *Calibrachoa* variety 'CA-2011-0404' (unpatented) and an unknown male *Calibrachoa* variety.

In summer 2010, an open pollination between the female variety 'CA-2011-0404' and an unknown male *Calibrachoa* variety was conducted in Stuttgart, Germany and seeds were obtained. The seeds were sown and plants were grown for evaluation. A plant was selected in May 2012 which had a pink and red flower color with a yellow throat and was subsequently named 'KLECA15294'. In May 2012, 'KLECA15294' was first vegetatively propagated by tip cuttings in Stuttgart, Germany. 'KLECA15294' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Pink and red flower color with yellow throat; and
2. A semi-trailing plant habit.

CROSS REFERENCE TO RELATED APPLICATIONS

Plant Breeder's Rights for 'KLECA15294' were applied for in Canada on Apr. 2, 2015 (Application number 15-8567). 'KLECA15294' has not been made publicly available or sold more than one year prior to the filing date of this application.

DESCRIPTION OF THE PHOTOGRAPH

This new *Calibrachoa* plant is illustrated by the accompanying photograph which shows the flowers and foliage of the plant. The photograph is of a three-month-old plant grown outdoors in Stuttgart, Germany in July 2013. The colors shown are as true as can be reasonably obtained by conventional photographic procedures.

DESCRIPTION OF THE NEW VARIETY

The following detailed descriptions set forth the distinctive characteristics of 'KLECA15294'. The data which define these characteristics were collected from asexual reproductions carried out in Stuttgart, Germany. Data was collected on twelve week-old plants grown in a controlled glass greenhouse in Stuttgart, Germany in May of 2015. Color references are to The R.H.S. Colour Chart of The Royal Horticultural Society of London (R.H.S.), 5$^{th}$ edition (2007).

Classification:
*Family.*—Solanaceae.
*Species.*—*Calibrachoa* sp.
*Common name.*—*Calibrachoa.*

Parentage:
*Female*.—Proprietary *Calibrachoa* 'CA 2011-0404' (unpatented).
*Male*.—Unknown.
Plant description:
*Life cycle*.—Annual.
*Form*.—Compact, tight.
*Habit*.—Semi-trailing.
*Height* (*from soil line to top of foliage*).—7.0 cm.
*Spread*.—18.0 cm.
Propagation: Vegetatively propagated.
*Type cuttings*.—Tip cuttings.
*Time to produce a rooted cutting*.—3 weeks.
Stems:
*Stem color*.—RHS 144B.
*Pubescence*.—Absent.
*Stem diameter*.—0.2 cm.
*Stem length*.—9.0 cm. From soil line to first node: 1.6 cm. Total length: 11.0 cm.
*Internode length*.—1.2 cm.
Leaves:
*Arrangement*.—Alternate, simple, sessile.
*Shape*.—Elliptic.
*Apex*.—Obtuse to slightly acute.
*Base*.—Attenuate.
*Margin*.—Entire.
*Surface*.—Smooth.
*Surface pubescence*.—Absent.
*Venation*.—Pinnate.
*Venation color*.—Upper surface: RHS 144C. Lower surface: RHS 144D.
*Length*.—2.5 cm.
*Width*.—0.8 cm.
*Color*.—Upper surface: RHS N137B. Lower surface: RHS N137D.
*Fragrance*.—Absent.
Flowers:
*Flowering habit*.—Single flowers.
*Flower type*.—Simple inflorescence.
*Flowering requirements*.—A minimum of light sun is required.
*Duration of flowers*.—7 days.
*Corolla*.—Smooth texture.
*Shape*.—Trumpet shaped.
*Fragrance*.—Absent.
Flower buds:
*Surface*.—Smooth.
*Length*.—2.0 cm.
*Diameter*.—0.7 cm.
*Shape*.—Irregular to oblong.
*Color*.—RHS 48C.
Peduncle:
*Length*.—2.2 cm.
*Diameter*.—0.1 cm.
*Color*.—RHS 144B.
*Texture*.—Smooth.
*Anthocyanin color*.—Absent.
Flower description:
*Flower depth*.—2.7 cm.
*Flower tube length*.—1.6 cm.
*Flower tube diameter*.—0.8 cm.
*Flower diameter*.—3.7 cm.
*Pedicel color*.—RHS 137D.
*Calyx*.—Funnel-shaped.
Sepals:
*Shape*.—Lanceolate.
*Apex*.—Acute.
*Margin*.—Entire.
*Length*.—1.7 cm.
*Diameter*.—0.6 cm.
*Sepal color*.—Upper surface: RHS 137B. Lower surface: RHS 137D.
Petals:
*Shape*.—Heart-shaped.
*Length*.—1.7 cm.
*Apex*.—Obverse.
*Margin*.—Entire, weak undulation.
*Base*.—Open and fused in the tube.
*Pubescence*.—Absent.
*Lobe length*.—1.5 cm.
*Lobe width*.—2.1 cm.
*Color*.—Lobe color: Upper surface: RHS 58C and RHS 45A. Lower surface: RHS 58D. Corolla tube color: Inner: RHS 6A. Outer: RHS 5C.
*Fragrance*.—Absent.
Reproductive organs:
*Stamen number*.—5. Anther color: RHS 10B. Filament color: RHS 10D. Pollen color: RHS 10A.
*Ovary*.—Placenta arrangement: Ovate. Pistil number: 1. Pistil length: 0.1 cm. Stigma color: RHS 144B. Style length: 0.9 cm. Style color: RHS 144D.
Fruit/seed set: Seed is sometimes observed but additional information is not available.
Disease/insect resistance: None observed.

COMPARISON WITH PARENTAL LINE AND KNOWN VARIETY

'KLECA15294' is distinguished from its female parent as described in Table 1:

TABLE 1

Comparison with Parental Line

| Trait | Variety 'KLECA15294' | Female parent 'CA-2011-0404' |
|---|---|---|
| Flower size | Large | Medium |
| Flower richness | Rich | Low |

'KLECA15294' is must similar to the *Calibrachoa* plant named 'KLECA10216' (U.S. Plant Pat. No. 22,893), also known as MINIFAMOUS Neo Pink+Red eye. Differences between the two varieties are described in Table 2:

TABLE 2

Comparison with Similar Variety

| Trait | Variety 'KLECA15294' | Commercial line 'KLECA10216' |
|---|---|---|
| Growth habit | Semi-trailing, compact | Semi-trailing, vigorous |
| Flower color | RHS 58C + RHS 45A | RHS 75C + RHS 61B |

We claim:

1. A new and distinct variety of *Calibrachoa* plant named 'KLECA15294' as illustrated and described herein.

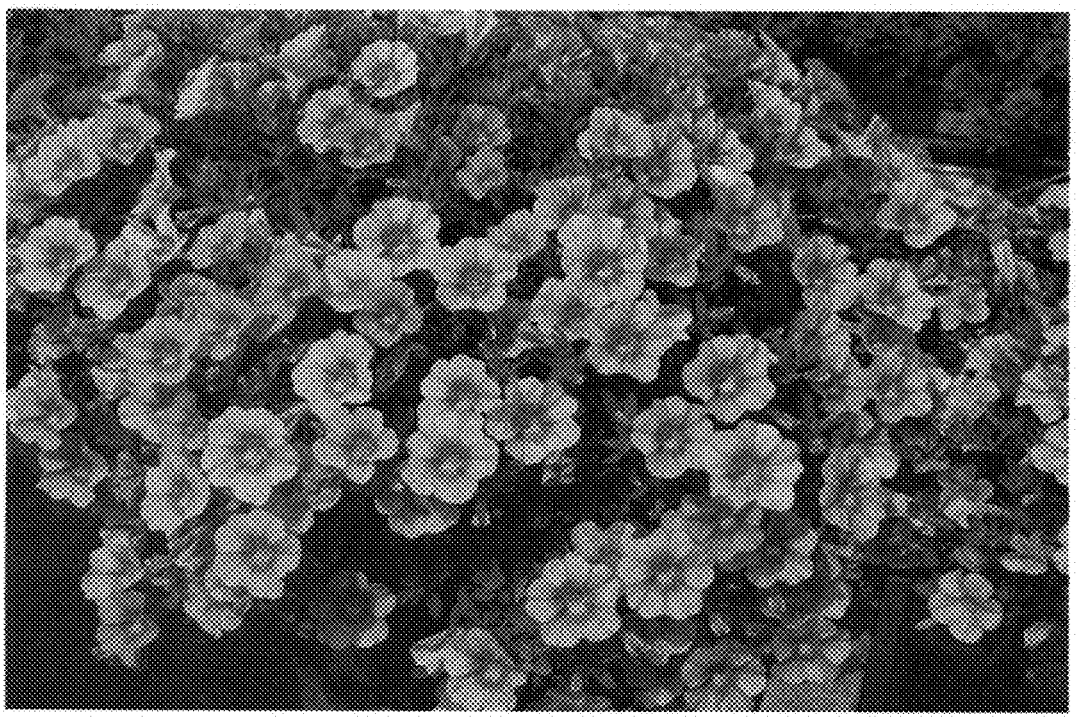

* * * * *